United States Patent [19]
Dillon

[11] Patent Number: 5,931,854
[45] Date of Patent: Aug. 3, 1999

[54] NASAL DILATOR

[76] Inventor: Michael M. Dillon, 8436 W. Piccadilly Rd., Phoenix, Ariz. 85037

[21] Appl. No.: 09/013,445

[22] Filed: Jan. 26, 1998

[51] Int. Cl.⁶ .............................. A61F 5/08; A61M 29/00; A61M 15/08; A62B 7/00
[52] U.S. Cl. ............... 606/204.45; 606/199; 128/209.18; 128/DIG. 26; 128/200.24
[58] Field of Search ......................... 128/200.24, 207.18, 128/DIG. 26; 606/199, 204.45

[56] References Cited

U.S. PATENT DOCUMENTS

| | | |
|---|---|---|
| 1,292,083 | 1/1919 | Sawyer . |
| 5,476,091 | 12/1995 | Johnson . |
| 5,479,944 | 1/1996 | Petruson . |
| 5,533,499 | 7/1996 | Johnson . |
| 5,533,503 | 7/1996 | Doubek et al. . |
| 5,718,224 | 2/1998 | Muchin ............................ 128/200.24 |
| 5,735,272 | 4/1998 | Dillon et al. ........................ 128/207.18 |
| 5,752,511 | 5/1998 | Simmons et al. ................... 128/207.18 |

*Primary Examiner*—Kimberly L. Asher
*Attorney, Agent, or Firm*—Parsons & Goltry; Robert A. Parsons; Michael W. Goltry

[57] ABSTRACT

An apparatus for preventing a nasal passage of a nose from constricting during breathing, the nose including a summit and a spaced-apart base presenting an orifice and an outer wall bounding a nasal passage, the outer wall having a substantially concave outer surface extending substantially from the summit to the base, the apparatus comprising a resilient body having a normal state, the resilient body engagable when flexed with the substantially concave surface of the nose extending longitudinally substantially from the summit to the base, the inherent tendency of the resilient body to assume the normal state to stabilize the outer wall substantially from the summit to the base and prevent the outer wall from drawing inwardly during breathing.

17 Claims, 2 Drawing Sheets

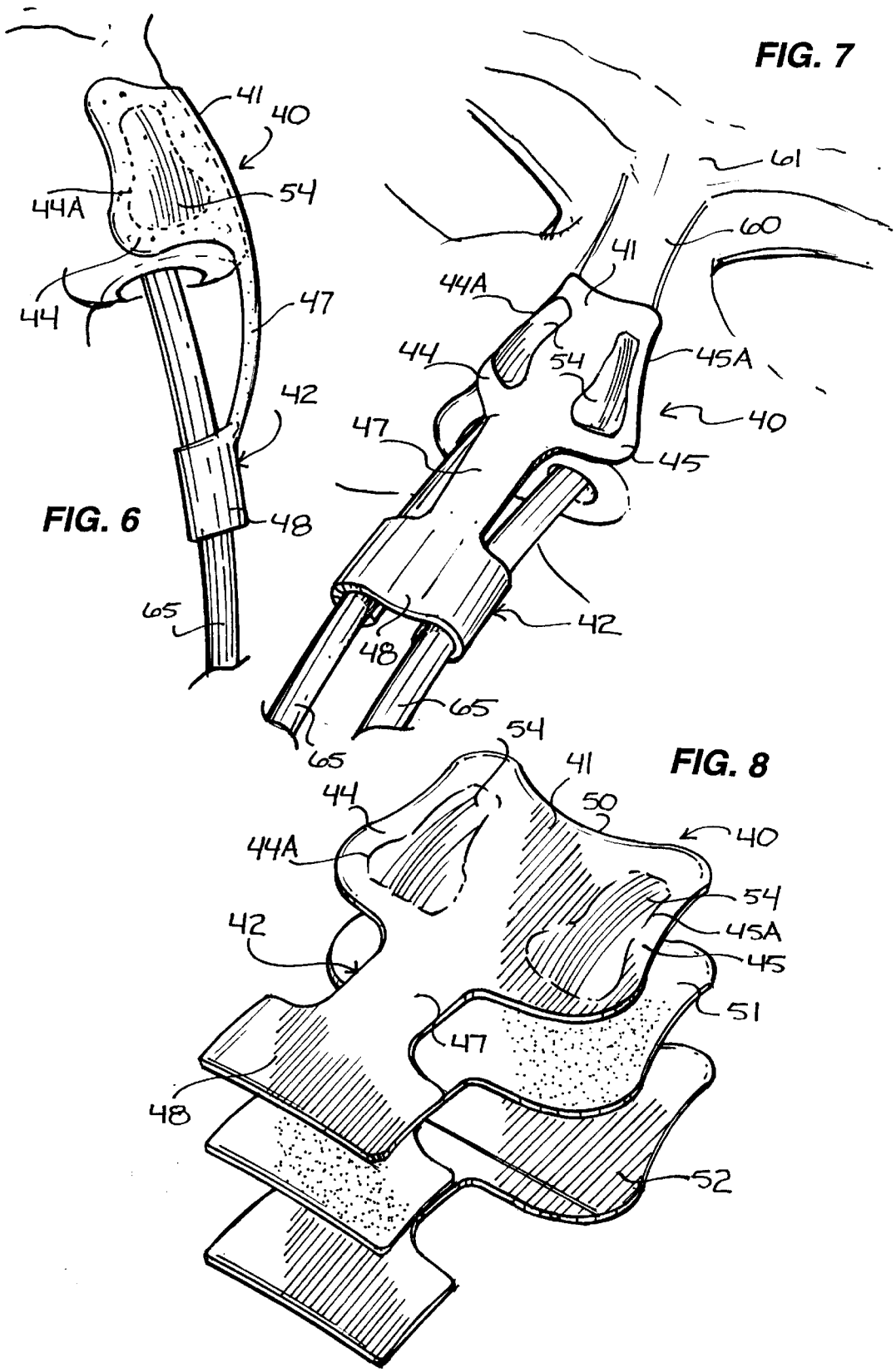

NASAL DILATOR

BACKGROUND OF THE INVENTION

1. Field of the Invention

This invention relates to dilators.

More particularly, this invention relates to nasal dilators.

In a further and more specific aspect, the instant invention relates to an apparatus for preventing a nasal passage of a nose from constricting during breathing.

2. Prior Art

A portion of the human population has some malformation of the nasal passages that makes breathing difficult. Examples of such malformations are a deviated septum and swelling due to allergic reactions. The lower portion of the nostril immediately above the entrance to the nostril is known as a vestibule. The vestibule tapers inwardly to a narrowed neck-like area called the ostium internum. Above the ostium internum the nasal passages widen. Nasal obstructions commonly occur at the ostium in individuals who have swelling due to allergic reactions, a deviated septum or similar condition. Commonly, the lateral wall at the ostium is loose with the result that the outer wall tissue draws in during the process of inhalation to substantially block the passage of air through the nasal passage.

Blockage of the nasal passages is obviously very frustrating. In particular, sustained mouth breathing over a long period of time may cause lung irritation due to the inhalation of foreign particles that would otherwise be filtered if the breath had been passed through the nose. Blockage of the nasal passages is particularly uncomfortable at night, since it is uncomfortable for many people who have such a problem to breathe through the mouth while asleep. Nasal blockage can lead to sleep disturbances and irregularities because those with such a condition may often wake during the night because of oxygen depletion.

The most common approach to a serious and chronic nasal blockage problem as described above is a surgical attempt to correct the malformation of the nasal passages. However, surgery is expensive and may not ultimately correct the problem.

As an alternative to surgery, nasal dilators for aiding breathing through the nose have been devised. One such nasal dilator includes generally elongated top and bottom rings which are spaced apart and connected together by a rear strut and a front strut. The front strut is longer than the rear strut and includes a bend therein formed at a position close to the front end of the bottom ring. When in place in the nasal passage, the top ring fits in the ostium within the nostril to prevent the tissue from being drawn in during inhalation, and to reduce extra flow resistance during exhalation. The bottom ring fits above the entrance to the nostril and serves to stabilize the position of the top ring within the nasal passage. One of these nasal dilators must be inserted into each nasal passage to provide unobstructed breathing.

However, these nasal dilators are not always effective because they are uncomfortable to wear and must be inserted within the nasal passages which can cause irritation and itching. In addition, these nasal dilators must be custom-made to fit each nasal passage of an individual.

Another known nasal dilator is comprised of a truss including a flexible strip of material having a first end region, a second end region and an intermediate segment. The first and second regions are adapted to engage the outer wall tissue of first and second nasal passages of the nose. The intermediate segment is configured to traverse a portion of the nose located between the first and second nasal passages. The truss member further includes first and second resilient bands secured to the strip of material adjacent opposite edges of the intermediate segment. The first and second resilient bands tend to return to their planar state. This motion acts to stabilize the outer wall tissue and thereby prevent the outer wall tissue of the first and second nasal passages from drawing in during breathing.

Although exemplary, this nasal dilator is difficult to construct, uncomfortable and un-adjustable. It has been noticed that during use, the first end region and/or the second end region disengage the outer wall tissue of the respective nasal passages requiring a user to repeatedly engage either the first end region and/or the second end region with the outer wall tissue of the respective nasal passages for realizing the benefits of this nasal dilator. It is evident that there is a continuing need for improved nasal dilators.

It would be highly advantageous, therefore, to remedy the foregoing and other deficiencies inherent in the prior art.

Accordingly, it is an object of the present invention to provide a new and improved apparatus for preventing the outer wall tissue of a nasal passage of a nose from drawing in during breathing.

Another object of the present invention is to provide an apparatus that is easy to construct.

And another object of the present invention is to provide an apparatus that is easy to use.

Still another object of the present invention is to provide an apparatus that is easy to install.

Yet another object of the instant invention is to provide an apparatus that is comfortable to wear.

Yet still another object of the instant invention is to provide an apparatus that is inexpensive.

And a further object of the invention is the provision of eliminating the discomfort commonly found among known nasal dilating apparatus.

Still a further object of the immediate invention is the provision of convenience.

SUMMARY OF THE INVENTION

Briefly, to achieve the desired objects of the instant invention in accordance with a preferred embodiment thereof, provided is an apparatus for preventing a nasal passage of a nose from constricting during breathing, the nose including a summit and a spaced-apart base presenting an orifice and an outer wall bounding a nasal passage, the outer wall having a substantially concave outer surface extending substantially from the summit to the base. Consistent with the foregoing, the apparatus of the present invention is generally comprised of a resilient body having a normal state. The resilient body is engagable when flexed with the substantially concave surface of the nose extending longitudinally substantially from the summit to the base. So engaged, the inherent tendency of the resilient body to assume the normal state operates to stabilize and pull the outer wall of the nose outwardly substantially from the summit to the base and prevent the outer wall from drawing inwardly during breathing and to dilate the nasal passage. In a preferred embodiment, the normal state of the resilient body may include a substantially arcuate state.

Consistent with the foregoing, associated methods may also be provided.

BRIEF DESCRIPTION OF THE DRAWINGS

The foregoing and further and more specific objects and advantages of the instant invention will become readily apparent to those skilled in the art from the following detailed description a preferred embodiment thereof taken in conjunction with the drawings in which:

FIG. 6 is a side elevational view illustrating a nasal tube holder as it would appear anchoring a tube to a patient in accordance with an alternate embodiment of the present invention;

FIG. 7 illustrates a perspective view of the nasal tube holder of FIG. 6 shown as it would appear anchoring a tube to a patient; and FIG. 8 illustrates an exploded perspective view of the nasal tube holder of FIG. 5.

DETAILED DESCRIPTION OF THE PREFERRED EMBODIMENT

Figures 1, 2, 3, 4, 5:
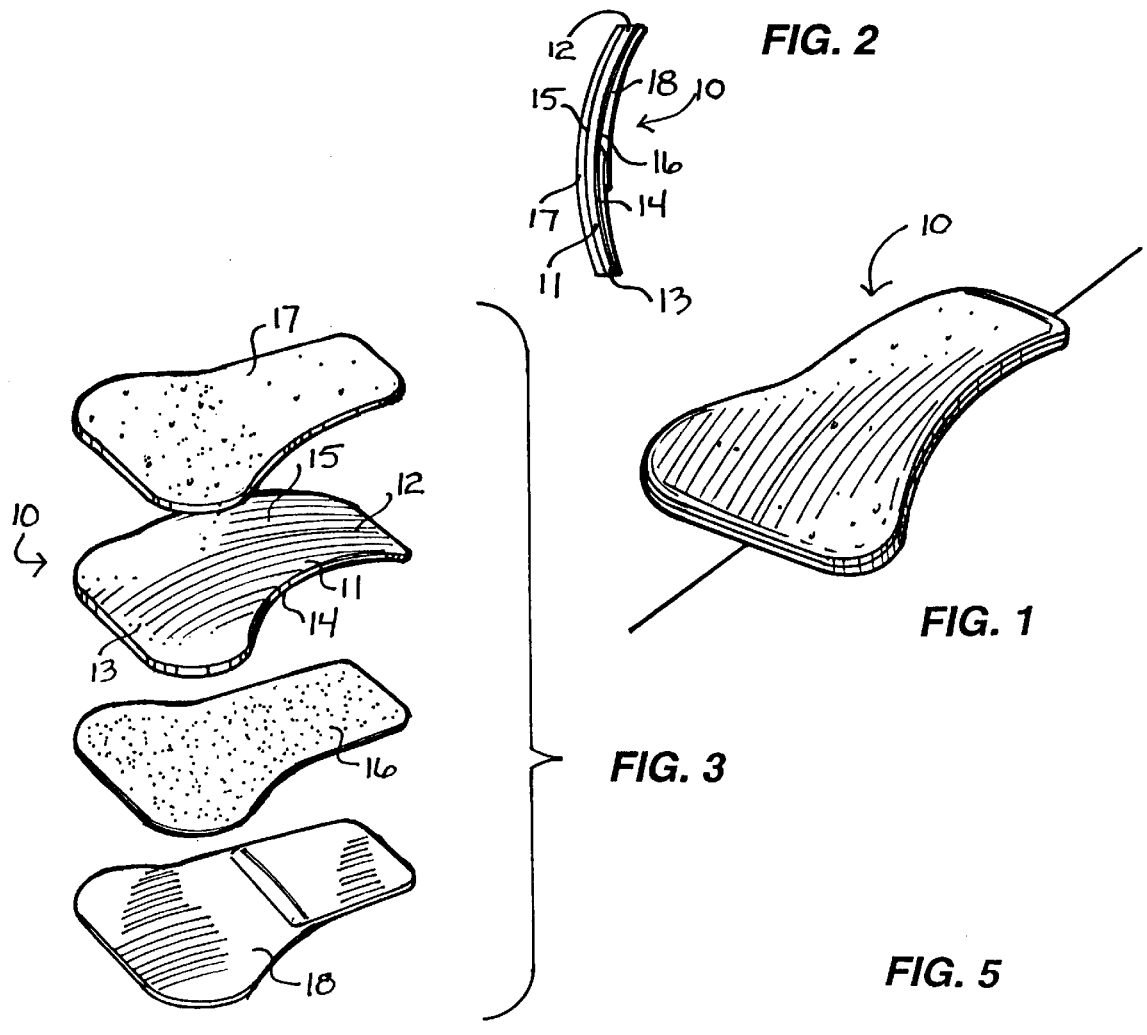
FIG. 1 illustrates a perspective view of an apparatus for preventing a nasal passage of a nose from constricting during breathing, in accordance with a preferred embodiment of the present invention.
FIG. 2 illustrates a side elevational view of the apparatus of FIG. 1.
FIG. 3 illustrates an exploded perspective view of the apparatus of FIG. 1.
FIG. 4 is a side elevational view illustrating the apparatus of FIG. 1 shown as it would appear engaged with a nose for preventing a nasal passage of the nose from constricting during breathing.
FIG. 5 is a front elevational view illustrating the apparatus of FIG. 1 shown as it would appear engaged with a nose for preventing a nasal passage of the nose from constricting during breathing.

The present invention provides, among other things, an apparatus and method for preventing a nasal passage of a nose from constricting during breathing. The apparatus of the present invention is rugged, easy to construct and may be installed selectively with a selected nasal passage as desired for providing an aggressive dilation of the nasal passage.

Turning now to the drawings, in which like reference characters indicate corresponding elements throughout the several views, attention is first directed to FIG. 1 illustrating a perspective view of an apparatus 10 for preventing a nasal passage of a nose from constricting during breathing, in accordance with a preferred embodiment of the present invention. With attention directed to FIG. 3 illustrating an exploded perspective view of apparatus 10, apparatus 10 is generally comprised of a body 11 constructed of a resilient material such plastic or other suitable material having shape memory characteristics. Having a normally substantially arcuate state, body 11 includes a first end 12, an enlarged second end 13, a normally substantially concave major surface 14 and a normally substantially convex major surface 15. Referring also to FIG. 2 illustrating a side elevational of apparatus 10, apparatus 10 further includes an adhesive substance or backing 16 carried by surface 14 and a cover 17 carried by or otherwise mounted with surface 15. Cover 17 forms a layer that covers surface 15 and is provided principally for protecting body 11 and may be constructed of gauze, microporous rayon, foam or other substantially flexible material. Adhesive backing 16 forms a layer that covers surface 14 of body 11. A removable liner 18 covers adhesive backing 16 and remains in place until apparatus 10 is to be used.

With attention directed to FIGS. 4 and 5, apparatus 10 is generally intended to be installed and engaged with a nose 20 of a wearer 21. For the purposes of anatomical orientation, nose 20 is of a substantially triangular form and projects from the center of the face of wearer 21 immediately above the upper lip. Nose 20 includes a summit or root 22 directed toward the forehead of wearer 21 and terminates downwardly with an inferior part or base 23 presenting two elliptical orifices 24. Nose 20 further includes first and second substantially opposing outer walls 25 that each bound a nasal passage 26 extending inwardly from each elliptical orifice 24, each outer wall 25 having a substantially concave outer surface 27 extending substantially from summit 22 to base 23.

In operation, liner 18 may be removed, such as by a user grasping and pulling liner 18 away from adhesive backing 16, to expose adhesive backing 16. The user may then engage apparatus 10 with one of the outer walls 25 of his or her nose 20 by directing substantially concave major surface 14 and adhesive backing 16 toward a selected outer surface 27 of nose 20 and, upon exertion of a force directed toward surface 15, flex body 11 to engage adhesive backing 16 with surface 27 of nose 20 with apparatus 10 to extend, once installed, longitudinally along outer surface 27 of nose substantially from summit 22 to base 23, with first end 12 of body 11 directed toward summit 22 and second end 13 of body 11 directed toward base 23. Upon installation, the inherent tendency of body 11 to assume its normal substantially arcuate state operates to stabilize and pull outer wall 25 outwardly longitudinally and substantially from summit 22 to base 23 along substantially the entire length of apparatus 10 from first end 12 to second end 13 of body 11. In this manner, apparatus 10 operates to aggressively dilate nasal passage 26, or otherwise place nasal passage 26 into a dilated condition, along substantially the entire longitudinal extend of nasal passage 26 from summit 22 to base 23 to thereby prevent outer wall 25 from drawing inwardly during breathing, thus increasing the volume of air that may pass through nasal passage 26 during respiration.

As shown in FIG. 4, body 11 defines the overall shape of apparatus 10. To this end, to maximize the adhesion of apparatus 10 with outer surface 27 of nose 20 for maximizing the ability of apparatus 10 to place the nasal passage 26 into an aggressively dilated condition, the shape of body 11 from first end 12 to enlarged end 13 is generally intended to conform substantially with substantially the entire outer surface 27 of outer wall 25 bounding nasal passage 26.

Referring now to FIGS. 6–8, illustrated is an alternate embodiment of the present invention setting forth a nasal tube holder 40. Referring specifically to FIG. 7, nasal tube holder 20 is generally comprised of a body 41 and a tube holding portion 42 depending therefrom. Body 41 has an elongate shape for bridging the human nose and includes opposing ends 44 and 45 engagable with opposing sides of the nose. Tube holding portion 42 includes a strip 47 depending generally perpendicularly from body 41 and terminating in an elongate pad 48 having a longitudinal axis generally perpendicular to strip 47 and parallel to body 41.

With additional reference to FIG. 1, nasal tube holder 40 is composed of three principle layers, a thin compliant body 50, an adhesive backing 51, and a liner 52 attached with adhesive backing 51 and removable therefrom to expose adhesive backing 51 prior to application of nasal tube holder 40 to a nose. Compliant body 50 carries at each end 44 and 45, such as in pouches 44A and 45A, an apparatus 54 of substantial similarity to apparatus 10 discussed previously. In this regard, with ends 44 and 45 engaged on either side of the nose as shown in FIGS. 6 and 7, each apparatus 54 will reside on the nose and dilate the nasal passages in a manner substantially identical to the manner of engagement and operation of apparatus 10 previously discussed. Adhesive backing 51 forms a layer which covers the back of compliant body 50.

Regarding FIG. 7, nasal tube holder 40 is shown applied to a nose 60 of a patient 61 with ends 44 and 45 adhered to opposing sides of nose 60, with each apparatus 54 shown engaged with one of the opposing sides of nose 60 for holding each nasal passage in a dilated condition consistent with the teachings set forth in combination with apparatus 10 previously discussed. Tube holding portion 42 depends from body 41 to a point below nose 60. Elongate pad 48 wraps about first and second nasal gastric tubes 65 securely attaching them to nasal tube holder 40 and anchoring it to nose 60. The dilation of each nasal passage by each apparatus 54 allows unobstructed breathing, and aids in keeping contact between tubes 65 and the delicate tissues inside nose 60 to a minimum.

The present invention has been described above with reference to a preferred embodiment. However, those skilled in the art will recognize that changes and modifications may be made in the described embodiments without departing from the nature and scope of the present invention. Various changes and modifications to the embodiment herein chosen for purposes of illustration will readily occur to those skilled in the art. To the extent that such modifications and variations do not depart from the spirit of the invention, they are intended to be included within the scope thereof which is assessed only by a fair interpretation of the following claims.

Having fully described the invention in such clear and concise terms as to enable those skilled in the art to understand and practice the same, the invention claimed is:

1. An apparatus for preventing a nasal passage of a nose from constricting during breathing,
the nose including a summit and a spaced-apart base presenting an orifice, an outer wall bounding a nasal passage, the outer wall having a substantially concave outer surface extending substantially from the summit to the base, and a bridge extending from the summit to the base,
the apparatus comprising:
a resilient body having a normal state, the resilient body engagable when flexed with the substantially concave surface of the nose extending longitudinally substantially from the summit to the base without traversing the bridge, the inherent tendency of the resilient body to assume the normal state to stabilize the outer wall substantially from the summit to the base and prevent the outer wall from drawing inwardly during breathing.

2. The apparatus of claim 1, wherein the normal state includes a substantially arcuate state.

3. The apparatus of claim 1, wherein the resilient body carries an adhesive substance for releasably securing the resilient body with the substantially arcuate surface of the nose.

4. The apparatus of claim 3, further including a liner covering the adhesive substance, said liner removable to expose the adhesive substance to permit the resilient body to be engaged with the substantially arcuate outer surface of the nose.

5. The apparatus of claim 3, wherein the adhesive substance is carried by a major surface of the resilient body.

6. The apparatus of claim 1, wherein the resilient body further includes a first end to direct toward the summit of the nose with the apparatus engaged with the substantially arcuate outer surface of the nose and an enlarged second end to direct toward the base of the nose with the apparatus engaged with the substantially arcuate outer surface of the nose.

7. The apparatus of claim 1, wherein the apparatus is carried by a nasal tube holder of a type for anchoring a tube in a nasal passage, the nasal tube holder comprising:
a body engagable with the nose, the apparatus being carried by the body; and
a tube holding portion depending from the body for engaging a tube and anchoring the tube within a nasal passage.

8. An apparatus for preventing a nasal passage of a nose from constricting during breathing,
the nose including a summit and a spaced-apart base presenting an orifice, an outer wall bounding a nasal passage, the outer wall having a substantially concave outer surface extending substantially from the summit to the base, and a bridge extending from the summit to the base,
the apparatus comprising:
a resilient body having a normally substantially arcuate state, the resilient body engagable when flexed with the substantially concave surface of the nose extending longitudinally substantially from the summit to the base without traversing the bridge, the inherent tendency of the resilient body to assume the normally substantially arcuate shape to urge the outer wall outwardly substantially from the summit to the base to dilate the nasal passage and prevent the outer wall from drawing inwardly during breathing.

9. The apparatus of claim 8, wherein the resilient body carries an adhesive substance for releasably securing the resilient body with the substantially arcuate surface of the nose.

10. The apparatus of claim 9, further including a liner covering the adhesive substance, said liner removable to expose the adhesive substance to permit the resilient body to be engaged with the substantially arcuate outer surface of the nose.

11. The apparatus of claim 8, wherein the resilient body further includes a first end to direct toward the summit of the nose with the resilient body engaged with the substantially arcuate outer surface of the nose and an enlarged second end to direct toward the base of the nose with the resilient body engaged with the substantially arcuate outer surface of the nose.

12. The apparatus of claim 9, wherein the adhesive substance is carried by a normally substantially concave surface of the resilient body.

13. The apparatus of claim 8, wherein the apparatus is carried by a nasal tube holder of a type for anchoring a tube in a nasal passage, the nasal tube holder comprising:
a body engagable with the nose, the apparatus being carried by the body; and
a tube holding portion depending from the body for engaging a tube and anchoring the tube within a nasal passage.

14. A method of preventing a nasal passage of a nose from constricting during breathing,
the nose including a summit and a spaced-apart base presenting an orifice, an outer wall bounding a nasal passage, the outer wall having a substantially concave outer surface extending substantially from the summit to the base, and a bridge extending from the summit to the base,
the method comprising the steps of:
providing a resilient body having a normal state; and
engaging the resilient body with the substantially concave surface of the nose substantially longitudinally extending substantially from the summit to the base without traversing the bridge, the inherent tendency of the resilient body to assume the normal state to stabilize the outer wall substantially from the summit to the base and prevent the outer wall from drawing inwardly during breathing.

15. The method of claim 14, wherein the step of providing a resilient body having a normal state further includes the step of providing a resilient body having a normal substantially arcuate state.

16. The method of claim 14, wherein the step of engaging the resilient body with the substantially arcuate surface of the nose further includes the step of:

providing an adhesive substance carried by the resilient body for releasably securing the resilient body with the substantially arcuate surface of the nose.

17. The method of claim 16, further including the step of providing a liner removable to expose the adhesive substance to permit the resilient body to be engaged with the substantially arcuate outer surface of the nose.

* * * * *